United States Patent [19]

Ritter

[11] Patent Number: 5,474,703
[45] Date of Patent: Dec. 12, 1995

[54] FLOCCULATING AGENT CONTAINING ALUMINUM AND A POLYBASIC CARBOXYLIC ACID

[75] Inventor: Günter Ritter, Bünde, Germany

[73] Assignee: Warner-Lambert Company, Morris Plains, N.J.

[21] Appl. No.: 395,212

[22] Filed: Feb. 27, 1995

[51] Int. Cl.$^6$ .................................................. C02F 1/54
[52] U.S. Cl. ........................ 252/181; 210/727; 210/728; 210/747
[58] Field of Search ..................... 210/727, 728, 210/723, 724, 747; 252/175, 180, 181

[56] References Cited

U.S. PATENT DOCUMENTS

| | | | |
|---|---|---|---|
| 2,862,880 | 12/1958 | Clemens | 210/728 |
| 3,544,476 | 12/1970 | Aiba et al. | 210/723 |
| 4,401,574 | 8/1983 | Farrington et al. | 210/728 |
| 4,655,934 | 4/1987 | Rose et al. | 210/728 |
| 5,250,189 | 10/1993 | Rey | 210/728 |
| 5,395,536 | 3/1995 | Brown et al. | 210/727 |

*Primary Examiner*—Neil McCarthy
*Attorney, Agent, or Firm*—Charles W. Almer, III

[57] ABSTRACT

A method of clarifying bodies of water and eliminating algal bloom caused by planktonic algae in water harboring biological systems is described using a novel flocculating agent prepared in an aqueous solution containing a combination of a monomeric or polymeric aluminum salt and a polybasic carboxylic acid; the method results in complete clarification of the body of water without harming fish that may be present; a preferred flocculating agent described includes a combination of polymeric aluminum hydroxy-chloride and L-(+)-tartaric acid.

6 Claims, No Drawings

FLOCCULATING AGENT CONTAINING ALUMINUM AND A POLYBASIC CARBOXYLIC ACID

FIELD OF THE INVENTION

The present invention relates to a method of clarifying bodies of water containing algal blooms caused by planktonic algae without harming fish that may be present by treating such waters with a flocculating agent.

BACKGROUND OF THE INVENTION

When fish are kept in garden pools or ponds, and in ponds in open surroundings, mass-multiplication of planktonic algae gives rise to algal blooms. This phenomena represents a serious problem both aesthetically and biologically. In addition, the problem can also occur albeit with a lesser intensity in outdoor ponds that do not harbor fish, and even in indoor holding systems, e.g. aquariums. Efforts have and are being made to combat these algal blooms.

Besides the use of herbicides, flocculating agents have been used in recent years for removing the photo-plankton quasi-mechanically. In particular, flocculating agents based on monomeric and polymeric aluminum salts have proved to be very effective.

Despite the useful effect that was achieved, i.e. the clarification of the water, the treatment of biological waters and fish-keeping systems with solutions of aluminum salts entails a number of disadvantages such as harmful side effects, their severity varying according to the aluminum salt chosen.

Thus, for example, large or repeated doses of aluminum salts will reduce the carbonate hardness, or alkalinity, of the water being treated by taking-up available $OH^-$ ions for the purpose of precipitating aluminum hydroxide.

Since dosing with aluminum salts entails the risk that the water will become insufficiently low in carbonate hardness or total alkalinity, the action taken to combat the algae will then become toxic for fish. This limits the single-application dose and the total number of doses that can be applied Many experiments have shown that, in fresh waters with a carbonate hardness of approximately 3° dH, or an alkalinity of approximately 1 mVal/l, or lower, there ceases to be any guarantee that the use of aluminum salts will be safe, and the occurrence of lethal toxic effects on fish becomes possible.

Even reducing the dosage of $Al^{3+}$ ions, e.g. from 8 mg/l to 2–3 mg/l, fails to bring about any significant reduction in the toxicity, given that the abovementioned chemical conditions of hardness and alkalinity prevail in the water. Although not wishing to be bound by theory, the reason for this resides in the mechanism of the toxic effect.

At the typical pH values that generally prevail, for example between about 6.5 and 8.5, the $Al^{3+}$ ion species present in solution no longer have toxic effects. However, so-called primary $Al(OH)_3$ flocs form at the beginning of the reaction in which the very sparingly soluble aluminum hydroxide is produced, and these primary flocs remain in colloidal solution.

These primary flocs, which are still positively charged, find their way onto the negatively charged gill tissues of the fish, and irritate the gills. The fish can suffocate as a result of an increase in the production of mucus by their gills.

These harmful effects become all the more powerful the longer the primary-floc formation phase lasts. Up to now, there was no way of selectively minimizing this vicious side effect of the $Al(OH)_3$ flocculation, as employed for eliminating algal blooms. Reliable protection was offered only by higher carbonate hardnesses, above 3° dH, or alkalinities above 1 mVal/l. However, most garden ponds exhibit lower values, especially in years of high rainfall, and thus turn a flocculation treatment with aluminum salts into a considerable and incalculable risk as far as the fish are concerned.

Some aluminum-free flocculating agents, e.g. with organic polymers, would certainly be usable under soft-water conditions, but would give rather unsatisfactory results as regards clarification.

There thus remains a need for an efficient flocculating agent to remove algal blooms in garden pools or ponds and other interior systems harboring fish without the serious toxicity effects on fish.

SUMMARY OF THE INVENTION

The present invention relates to the object of minimizing the harmful effects associated with the flocculation treatment of algal blooms by means of polymeric aluminum hydroxychlorides, e.g. with the empirical formula $Al_2(OH)_5Cl$. The present invention concerns the surprising finding that addition of organic carboxylic acids that have two or more protons brings about significant improvements and beneficial effects when combined with an aluminum salt.

Accordingly, the present invention is a new flocculating agent containing an aqueous solution of a monomeric or polymeric aluminum salt and a polybasic organic carboxylic acid in a molar ratio of aluminum ion to carboxylic acid of about 0.5:1 to about 50:1.

A second aspect of the present invention is a method of eliminating algal bloom in waters harboring biological systems comprising treating said waters with an effective amount of a flocculating agent comprising an aqueous solution of a monomeric or polymeric aluminum salt and a polybasic organic carboxylic acid in a molar ratio of aluminum ion to carboxylic acid of about 0.5:1 to about 50:1.

Another aspect of the present invention is a method of flocculating planktonic algae in fresh waters down to a carbonate hardness of about 1° dH and an alkalinity of about 0.36 mVal/l without harming fish which comprises treating said waters with an effective amount of a flocculating agent as described above.

Still another aspect of the present invention is a method of clarifying a body of water contaminated with an algal bloom comprising treating said body of water with an effective amount of a flocculating agent as described above.

DETAILED DESCRIPTION OF THE PREFERRED EMBODIMENTS

The invention describes novel flocculating agents for eliminating bloom phenomena in waters harboring biological systems, as caused by planktonic algae.

The agents contain an aluminum salt, which may be monomeric or polymeric, and a polybasic organic carboxylic acid, in molar ratios (Al:carboxylic acid) of 0.5:1 to 50:1, preferably 2:1 to 10:1.

The compositions of the agents are adjusted with a view to obtain the desired product range, and to ensure that each specific combination will be stable. The quantity of organic acid necessarily follows from the dosage requirement, and from the composition of the agent in question.

Applied in the dosages specified, the agents according to the invention enable the following novel effects to be achieved:

1. Flocculation of planktonic algae in fresh waters (algal bloom) is possible without harming fish, down to carbonate hardnesses of 1° dH and alkalinities of 0.36 mVal/l.
2. Flocculation is accompanied by a synergistic effect which
   a) accelerates floc formation,
   b) reduces the dosages of aluminum necessary for achieving comparably good clarification results (especially when the pH is below 8.0),
   c) and, by virtue of the smaller quantity of $Al^{3+}$ ions, results in reduced depletion of the carbonate hardness, or alkalinity.

The flocculating agent of the present invention is a combination of monomeric or polymeric aluminum salts with a polybasic carboxylic acid.

A monomeric or polymeric aluminum salt includes a trivalent aluminum salt in monomeric or polymer form. The preferred salt is aluminum hydroxy-chloride in both monomeric and polymeric form. Also of value are, for example, non-polymeric aluminum salts such as aluminum chloride or aluminum sulfate. These salts are all commercially available.

A polybasic carboxylic acid is an organic carboxylic acid having at least two active protons. Included among polybasic organic carboxylic acids, are those commercially available and, as examples which have proved suitable as flocculating agents with aluminum salts are:

citric acid;

glycolic acid;

tartaric acid;

maleic acid;

hydroxymaleic acids;

hydroxytartaric acids;

malonic acid;

malic acid;

lactic acid (α-hydroxypropionic acid);

tartronic acid;

sugar acids, such as gluconic acid;

saccharic acid;

glucuronic acid;

mucic acid; and mannosaccharic acid.

Citric acid and, especially, tartaric acid bring about a very pronounced lowering of the toxicity limit that is associated with the carbonate hardness or alkalinity, i.e. from CH= 3° dH, or alkalinity=1.1 mVal/l to CH=1° dH, or alkalinity=0.36 mVal/l An optimized solution of polymeric aluminum hydroxy-chloride, containing tartaric acid, can be used for flocculating algae even in water with a carbonate hardness of 0.5° dH, or an alkalinity of 0.18 mVal/l, without harming garden-pond fish (koi, goldfish, golden carp and the like).

Of all the above-mentioned acids, L-(+)-tartaric acid, in combination with polymeric aluminum hydroxychloride has achieved the best results.

In contrast, concentrated solutions of polymeric aluminum hydroxy-chloride, on their own or in diluted form, react very sensitively to further additions, and such reactions are accompanied by precipitation effects and extremely large increases in viscosity, even proceeding as far as solidification.

A solution containing only aluminum hydroxychloride, applied in a dosage giving the same aluminum concentration, caused toxic effects that were lethal even at carbonate hardnesses of 2° dH, or alkalinities of 0.7 mVal/l.

The mixtures, according to the present invention, for example, of polymeric aluminum hydroxy-chloride and a polybasic organic carboxylic acid exhibit yet a further surprising effect.

In addition to the significant lowering of the carbonate hardness limit associated with the onset of toxicity, the use of the mixtures according to the invention is also accompanied by a flocculation synergism.

In cases involving algal blooms of equal intensity and pH values in the region of 7.5, the clarifying effect obtained with 50% of the $Al^{3+}$ dosage in combination with a polybasic carboxylic acid already shows 60% of the effect obtained with the 100% dosage of the polymeric $Al_2(OH)_5Cl$ solution alone. Comparable results were also achieved with non-polymeric aluminum salts, e.g. $AlCl_3 \cdot 6H_2O$ and $Al_2(SO_4)_3 \cdot 18H_2O$.

The agents according to the invention were unknown until now, as were the surprising effects that are achievable through their use.

The dosage of the agents that have been described is generally selected with a view to ensuring that 0.5 to 50 mg/l $Al^{3+}$, preferably 2 to 10 mg/l $Al^{3+}$ are introduced into the water treated.

The following examples are illustrative of the present invention and are not to be construed as limiting thereon.

EXAMPLES

Agent Examples 1–3

500 ml of a concentrated solution of $Al_2(OH)_5Cl \cdot 2-3H_2O$ (50% strength solution, 23.5% $Al_2O_3$) were mixed with 1. 50 g L-(+)-tartaric acid
2. 100 g L-(+)-tartaric acid
3. 150 g L-(+)-tartaric acid and demineralized water, stirring all the while, and each of these mixtures was thus diluted to 1 liter.

The resulting solutions were clear and slightly viscous; they exhibited long-term stability and can be used for flocculating planktonic algae.

Use Example

One of the agents itemized under Agent Examples was added to garden pond water that had become discolored to the extent of becoming green and non-transparent as a result of an algal bloom, the dosage applied being 500 ml per 10,000 liters of pond water.

After 24 hours, the water was clarified to the highest possible degree, and the flocculated-out algae settled.

The dosage specified above, and twice this dosage (1,000 ml per 10,000 l) can be applied without endangering pond fish, down to carbonate hardnesses of 1° dH, or alkalinities of 0.36 mVal/l.

I claim:

1. A flocculating agent comprising an aqueous solution of a polymeric aluminum hydroxy-chloride and a polybasic organic carboxylic acid in a molar ratio effective to flocculate planktonic algae in fresh waters having a carbonate hardness greater than about 0.5° dH and an alkalinity greater than about 0.18 mVal/l.

2. The agent of claim 1 wherein the polybasic organic carboxylic acid is selected from the group consisting of citric, glycolic, tartaric, maleic, hydroxymaleic, hydroxytartaric, malonic, malic, lactic, tartronic, gluconic, saccharic, glucuronic, mucic, mannosaccharic and a mixture thereof.

3. The agent of claim 2 wherein the polybasic carboxylic acid is citric or tartaric acid.

4. The agent of claim 1 wherein the molar ratio of aluminum to carboxylic acid is about 2:1 to about 10:1.

5. The agent of claim 1 comprising an aqueous solution of polymeric aluminum hydroxy-chloride and L-(+)-tartaric acid.

6. The agent of claim 5 wherein the molar ratio of aluminum ion to tartaric acid is about 2:1 to about 10:1.

* * * * *